United States Patent [19]
Simeroth et al.

[11] Patent Number: 5,150,601
[45] Date of Patent: Sep. 29, 1992

[54] FLUID SAMPLING FOR GAS CHROMATOGRAPH WITH MODIFIED SAMPLING VALVE

[75] Inventors: David L. Simeroth, Lake Jackson, Tex.; David S. Brink, Antioch, Calif.; Reid S. Willis, Martinez, Calif.; Dale J. Backlund, Concord, Calif.

[73] Assignee: The Dow Chemical Company, Midland, Mich.

[21] Appl. No.: 631,553

[22] Filed: Dec. 21, 1990

[51] Int. Cl.$^5$ .............................................. G01N 1/14
[52] U.S. Cl. ................................. 73/23.41; 73/863.11; 73/863.83
[58] Field of Search ................. 73/23.39, 23.35, 23.41, 73/23.42, 863.73, 863.83, 863.84, 863.11

[56] References Cited

U.S. PATENT DOCUMENTS

| | | | |
|---|---|---|---|
| 3,885,438 | 5/1975 | Harris et al. | 73/863.81 |
| 4,128,008 | 12/1978 | Linenberg | 73/864.83 |
| 4,356,733 | 11/1982 | Braunweiler | 73/863.11 |
| 4,872,334 | 10/1989 | Watanabe | 73/23.24 |
| 4,957,706 | 9/1990 | Romette et al. | 73/863.73 |

*Primary Examiner*—Hezron E. Williams
*Assistant Examiner*—Michael Brock
*Attorney, Agent, or Firm*—Timothy S. Stevens

[57] ABSTRACT

A new use for a process gas chromatography liquid injection valve of the Bendix type, i.e., a valve having a distal heated vaporization chamber, a central sample chamber, a valve stem bore intersecting both chambers, a radially grooved valve stem positioned within the valve stem bore and an air actuator for moving the valve stem back and forth in the valve stem bore. The heated vaporization chamber is removed and is not used. Instead, a carrier gas is now flowed through the remaining chamber of the valve. The valve is mounted on a process vessel or a process conduit (and not on a gas chromatograph) so that the valve stem of the valve now can be extended from the valve and into the process liquid in the process vessel or conduit. The groove of the valve stem fills with sample and then the valve stem is retracted into the valve so that the groove is positioned within the remaining chamber, i.e., what was used as a sample chamber is now is used as a vaporization chamber. The liquid in the groove can then evaporate into the carrier gas and be carried to a gas chromatograph or other analyzer.

3 Claims, 3 Drawing Sheets

FLUID SAMPLING FOR GAS CHROMATOGRAPH WITH MODIFIED SAMPLING VALVE

BACKGROUND OF THE INVENTION

On-line process gas chromatography of liquid process streams generally involves piping a side stream of the liquid process stream to a gas chromatograph. This side stream of the liquid process stream is called the sample stream. The gas chromatograph is usually equipped with a process sample injection valve such as the well known Bendix valve, now available from Process Analytics Combustion Engineering Company, Lewisburg, W. Va., as Model 35267491-2-1. The first paragraph of the Detailed Description of the Invention section of this specification describes the features and operation of this type of valve in reference to FIG. 1.

This type of on-line process gas chromatography was an important advancement in the art and it is believed to be used extensively in industry. However, several problems remain with its use, including the following. First, the piping or tubing of the sample stream can become plugged. This is not at all uncommon and requires backflushing or other means to clear the sample piping or tubing so that the gas chromatograph can be placed back into service. Second, there is a time lag due to the residence time of the sample flowing through the sample pipe or tube. If the gas chromatograph must be situated some distance from the process stream, as is often necessary for practical reasons, then this time delay can become significant. Third, it is often necessary to pump the sample stream. The sample stream pump requires maintenance and can break down.

SUMMARY OF THE INVENTION

The present invention, to a large degree, solves the above mentioned problems. The present invention comprises a new use for the above described type of injection valve. The distal heated vaporization chamber of this type of valve is removed. A carrier gas is now flowed through the remaining chamber of the valve. The valve, minus the vaporization chamber, is mounted on a process vessel or a process conduit (and not on a gas chromatograph) so that the valve stem of the valve now can be extended from the valve and into the process liquid in the process vessel or conduit. The groove of the valve stem fills with sample and then the valve stem is retracted into the valve so that the groove is positioned within what was used as a sample chamber but now is used as a vaporization chamber. The liquid in the groove can then evaporate into the carrier gas and be carried to an analyzer such as a gas chromatograph or a mass spectrometer. Preferably, a means is used for heating the carrier gas flowing through the valve or for heating the valve body so that the liquid in the groove evaporates more rapidly.

DETAILED DESCRIPTION OF THE INVENTION

Figure 1:
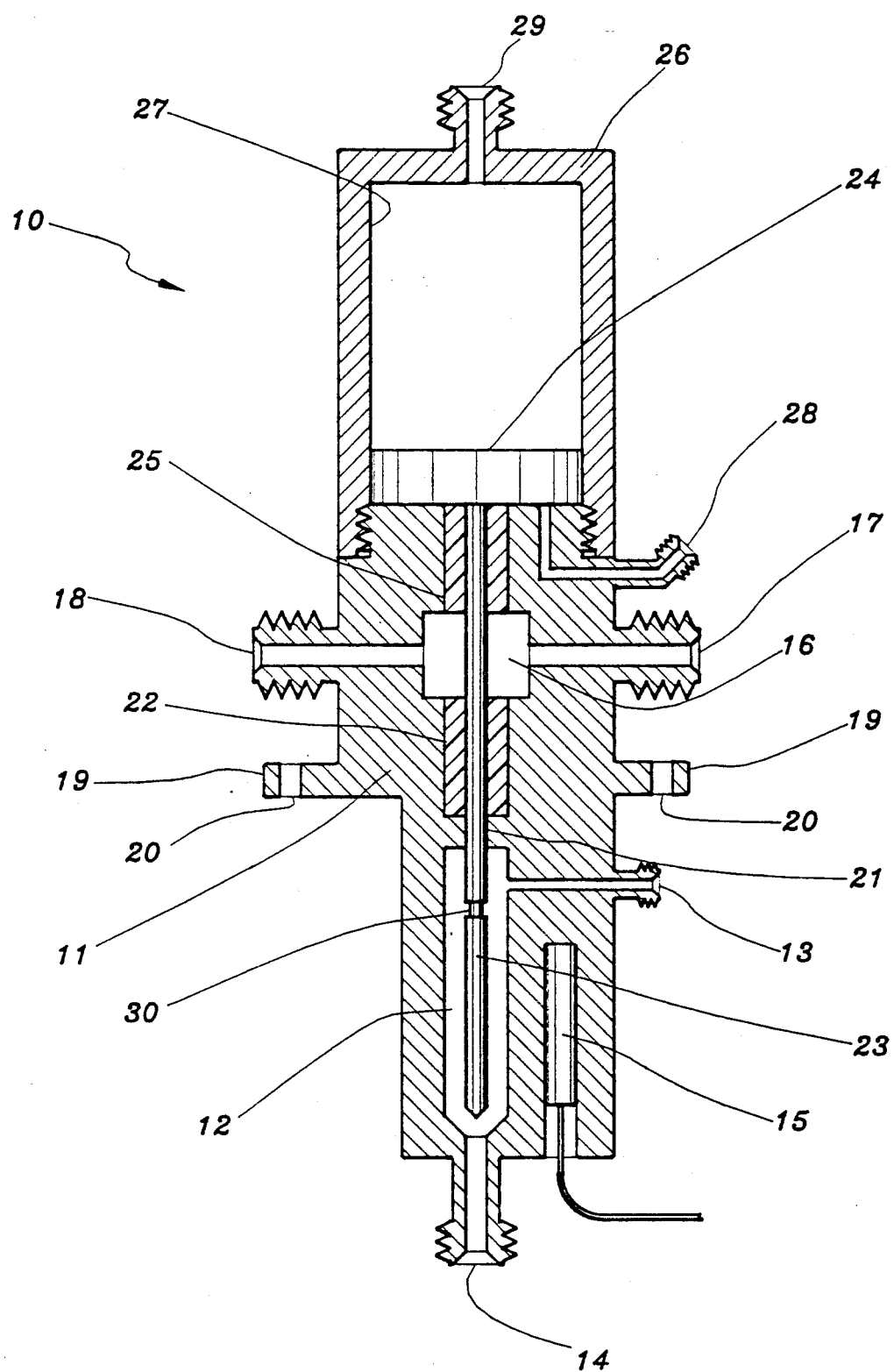
FIG. 1 is a cross-sectional side view of a prior art process gas chromatography liquid sample injection valve showing the groove of the valve stem positioned in the vaporization chamber of the valve.

Referring now to FIG. 1, therein is shown a cross-sectional side view of a prior art process gas chromatography liquid sample valve 10. The valve 10 shows the general features of the well known Bendix valve, now available from Process Analytics Combustion Engineering Company, Lewisburg, W. Va., as Model 35267491-2-1 or the Mess Und Apparatetechnik valve Model 101-280, Munchen, Germany. The valve 10 has a body 11. The body 11 defines a distal vaporization chamber 12, a carrier gas inlet port 13 and a carrier gas outlet port 14. An electrical heater 15 heats the vaporization chamber 12. A gas chromatography carrier gas is flowed into the port 13 and a gas chromatography column is connected to the port 14. The body 11 also defines a central sample chamber 16, a sample inlet port 17 and a sample outlet port 18. A process liquid is flowed into the port 17, through the chamber 16 and then out the port 18. The body 11 also defines a mounting flange 19 having bolt holes 20 so that the valve 10 can be mounted to a gas chromatograph. The body 11 also defines a valve stem bore 21 which intersects the cavity 12 and the cavity 16. A seal 22 is positioned in the bore 21 between the chamber 12 and the chamber 16. A valve stem 23 is positioned in the valve stem bore. One end of the valve stem 23 is connected to a piston 24. A seal 25 is positioned in the bore 21 between the chamber 16 and the piston 24. A cylinder cap 26 is threaded to the body 11. The cylinder cap 26 defines a piston bore 27. A compressed air port 28 in the body 11 leads to the bottom side of the piston 24. A compressed air port 29 in the cap 26 leads to the top side of the piston 24. The valve stem 23 has a radial groove 30 cut into it. When compressed air is flowed into the port 28, then the piston 24 and the valve stem 23 is slid upwards so that the groove 30 is positioned within the sample chamber 16. The, groove 30 fills with liquid sample flowing through the chamber 16. When compressed air is flowed into the port 29, then the piston 24 and the valve stem 23 are slid downward to the position shown so that the groove 30 is positioned within the heated vaporization chamber 12. The liquid sample contained in the groove 30 evaporates into the carrier gas flowing through the chamber 12 and is carried into the column connected to the port 14.

Figure 2:
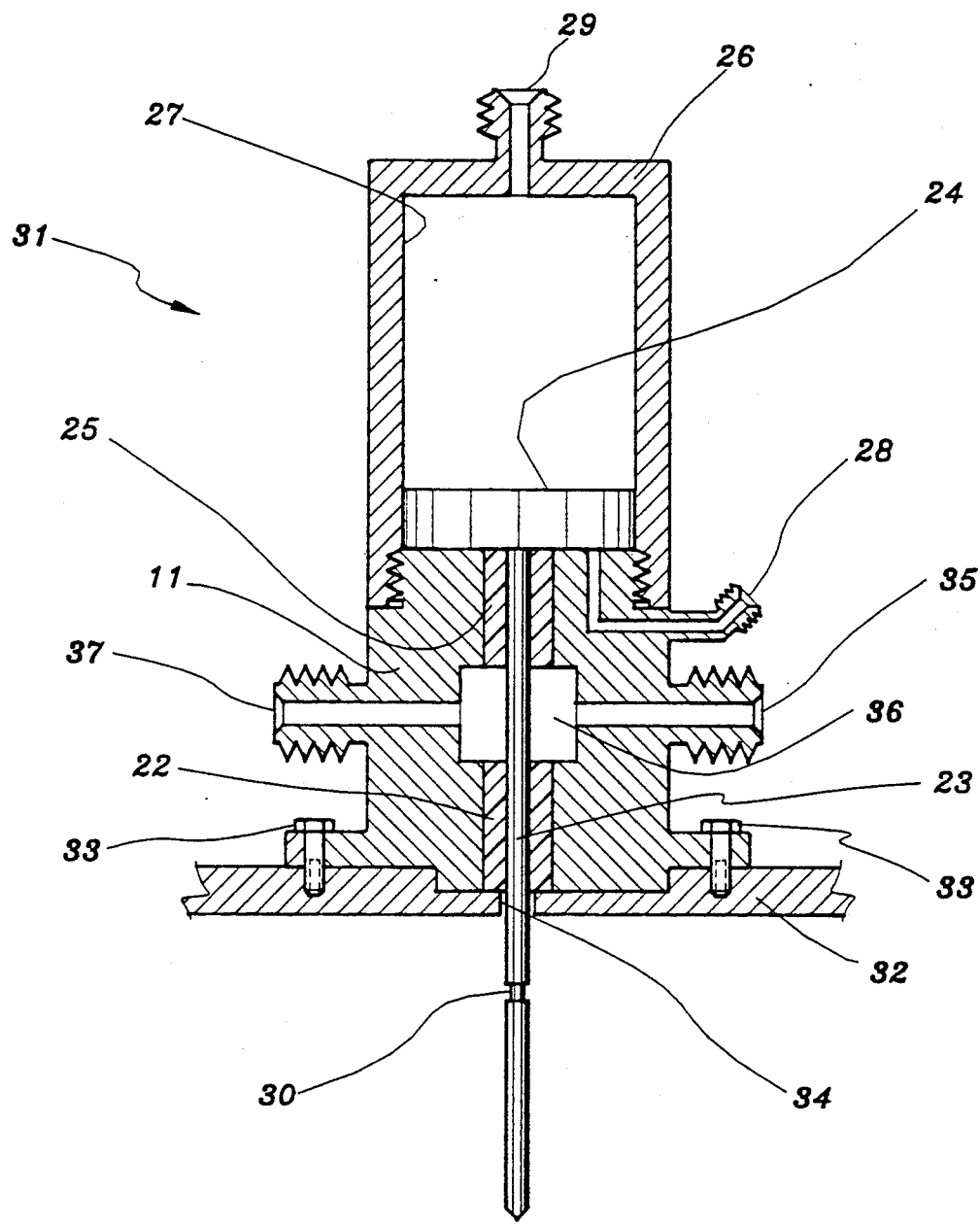
FIG. 2 is a cross-sectional side view of a valve like the valve shown in FIG. 1 but with the vaporization chamber removed, the remainder of the valve mounted to a process vessel, the groove of the valve stem being positioned within the vessel.
Figure 3:
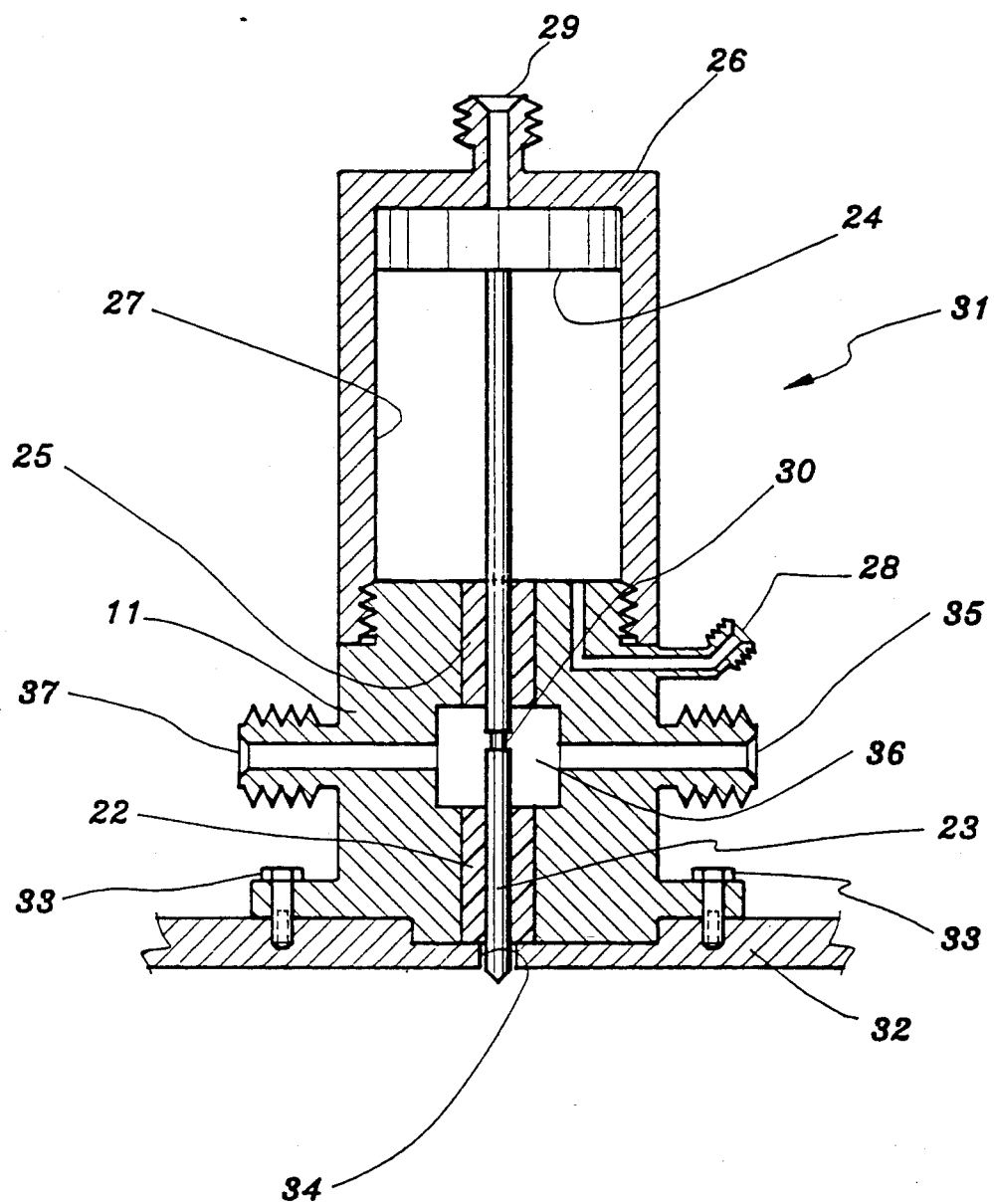
FIG. 3. is a cross-sectional side view of the valve shown in FIG. 2 but with the groove of the valve stem being positioned within the remaining chamber of the valve.

Referring now to FIG. 2, therein is shown a cross-sectional side view of a valve 31 of the present invention which is like the valve 10 shown in FIG. 1 but with the lower portion of the valve 10 removed. The valve 31 is attached by bolts 33 to a wall 32 of a process vessel. The process vessel contains a process liquid. The elements of the valve 31 whose function are the same as the valve 10 are referred to by the same reference numerals as were used to describe the valve 10. The wall 32 has a hole 34 through which the valve stem 23 extends. A stream of carrier gas is flowed into a carrier gas inlet port 35, through a vaporization chamber 36, and then out an outlet port 37 to an analyzer such as a gas chromatograph or a mass spectrometer. The groove 30 in the valve stem 23 is extended from the valve 31 and into the process liquid contained by the wall 32 so that the process liquid fills the groove 30. A supply of compressed air is directed into the port 28 to cause the piston 24 and the valve stem 23 of the valve 31 to slide upwards to the position shown in FIG. 3. Referring now to FIG. 3, the groove 30 is now positioned within the vaporization chamber 36. The process liquid in the groove 30 evaporates into the carrier gas flowing through the chamber 36 and is carried to the analyzer.

The discussion of the above two paragraphs teaches that the present invention is a new use for an existing type of valve. The sample chamber 16 of the prior art valve 10 shown in FIG. 1 is instead used as the vaporization chamber 36 in the valve 31 of the present invention as shown in FIGS. 2 and 3. The valve stem 23 of the prior art valve 10 shown in FIG. 1 remains within the valve 10 but as shown in FIG. 2, the valve stem 23 of the present invention extends from the valve 31. The valve 31 is mounted on the wall 32 of a process vessel and not on a gas chromatograph. Thus, no process liquid is piped to the valve 31 which eliminates any possibility of a plugged sample line and which eliminates the need for a sample pump. The flow of carrier gas from the port 37 to the analyzer can be rapid because it is a gas flow. Thus, there is little delay between the taking of the sample and its delivery to the analyzer.

The valve 31 of FIG. 2 is shown attached to the wall 32 of a process vessel. However this is not critical, e.g., the valve 31 could have been attached to the wall of a process pipe. When the valve 31 is attached to the wall of a process pipe, then it is preferable to mount it to the bottom of the pipe if there is any possibility that the pipe may not be completely filled with the process liquid. Referring now to FIG. 2, the hole 34 preferably is relatively large to aid in gaining a representative sample but not so large that the seal 22 is not retained in the body 11 if such retaining function is necessary. The above described Mess Und Apparatetechnik valve has a tapered seal 22 which is preferably arranged to extend through the hole 34, i.e., when this valve is used, then the edge of the hole 34 need not be used to retain the seal 22.

Referring now to FIG. 2, it is often preferable to heat the carrier gas flowing into the port 35 and to wrap the body 11 with thermal insulation or to wrap the body 11 with heating tape and then with thermal insulation so that the liquid in the groove positioned within the chamber 36 will evaporate more rapidly. Alternatively, an electrical heater can be embedded within the body 11 or other means used for heating the body 11 for the same purpose. However, the cap 26 is preferably not wrapped with thermal insulation so that it can operate at a lower temperature than the body 11. The valve stem 23 is preferably of round cross-section. However, this is not critical, e.g., the valve stem could have been of square cross-section. The groove 30 in the valve stem 23 is preferably a radial groove as shown. However, this is not critical and the term groove is intended to include a longitudinal groove or cut in the valve stem, a hole in the valve stem or other such means. Referring now to FIG. 3, preferably the temperature of the body 11 defining the vaporization chamber 36 is maintained above the atmospheric pressure boiling point of the process liquid so that the process liquid in the groove 30 evaporates rapidly into the carrier gas. The term evaporate means to change from a liquid phase into a gas or vapor phase. Preferably, the tube carrying the evaporated sample to the analyzer is heat traced to prevent condensation of the evaporated sample in the tube. In the case of the following example, it is known that the tube can be six feet long if it is one sixteenth inch outside diameter, forty thousandths inch inside diameter stainless steel tubing and it is believed that this tube could have been twenty feet long without seriously degrading the chromatogram.

EXAMPLE 1

A Process Analytics Combustion Engineering Company valve Model 35267491-2-1 is modified, as generally shown in FIG. 2, by removing its vaporization chamber and mounting flange portion leaving the valve stem seal exposed and unsupported. A three quarter inch thick, four and one half inch diameter steel disk is machined with a three diameter hole in its center from one face to the other face. The first diameter being 0.567 inch for a depth of three sixteenths inch, the second diameter being 0.500 inch for an additional depth of 0.367 inch, the third diameter being one quarter of an inch for the remaining depth of 0.195 inch. The face of the disk having the 0.567 inch diameter opening is drilled and tapped for #6-32 tpi (threads per inch) screws, nine sixteenths inch deep, at twelve, three, six and nine o'clock, 0.625 inch from the center of the three diameter hole. Mounting holes, nine thirty-seconds of an inch in diameter, are drilled through the disk at twelve, three, six and nine o'clock, 1.77 inch form the center of the three diameter hole. The remainder of the Process Analytics Combustion Engineering Company valve Model 35267491-2-1 is attached to the disk with 6-32 screws, the seal of the valve being supported by the first two diameters of the central hole of the disk. The cylinder cap of the valve is removed and discarded. A new cylinder cap is made from aluminum to duplicate the original cap but to be longer, i.e., 2.89 inch, to provide for a longer piston stroke. The valve stem is removed and discarded. A new valve stem is made from stainless steel to duplicate the original valve stem but to be longer, i.e., 4.5 inch. The groove is machined to contain one microliter of sample liquid. A three and one quarter inch long, three and one quarter inch wide opening is made in the center of a three inch inside diameter, two foot long pipe spool. A one side curved, one side flat saddle of steel is welded into this opening so that the curved side of the saddle coincides with the curve of the pipe spool. The flat side of the saddle is drilled through at its center with a one half inch diameter hole. The flat side of the saddle is drilled and tapped, at one thirty, four thirty, seven thirty, and ten thirty o'clock, for ¼ inch 20 tpi bolts, one half inch deep, 1.77 inch form the center of the one half inch diameter hole. The thickness of the saddle at the one half inch diameter hole is about 0.32 inch. The valve is mounted on the saddle with ¼ inch 20 tpi bolts so that the valve stem extends through the one half inch diameter hole in the saddle.

The pipe spool valve combination is assembled in a chemical process so that process liquid flows through the spool. The spool is mounted with the valve being down and the longitudinal axis of the spool being angled somewhat downward because the process liquid flowing through the spool does not fill it completely. The valve body is wrapped with thermal insulation. A supply of three hundred degree centigrade helium at three hundred milliliters per minute at a gauge pressure of twelve pounds per square inch is flowed through the remaining chamber of the valve to a Varian 3700 gas chromatograph. The gas chromatograph is equipped with a split injector having a split ratio of 75:1 and a thirty meter long, eight tenths millimeter internal diameter capillary column having a DB-225 stationary phase. The column oven temperature of the gas chromatograph is one hundred and fifty degrees centigrade. The detector is a flame ionization type operated at two hundred and fifty degrees centigrade. An integrator-recorder is connected to the gas chromatograph to record and integrate chromatograms. The valve stem is extended into the process liquid flowing through the spool for eight seconds and then withdrawn. The integrator-recorder is started. The integrator-recorder plots a chromatogram showing fourteen peaks eluting between 0.92 minutes and 10.77 minutes, the peak eluting at 5.85 minutes having a peak area of 98.794 percent of the total area for all of the peaks. From experience it is known that this peak is the intended product of the process and that the purity of the process liquid is within specifications.

EXAMPLE 2

This example teaches a procedure for modifying the Mess Und Apparatetechnik Model 101-280 valve according to the present invention. First, the "vaporizer cylinder" portion of this valve is removed from the remainder of the valve. Second, the "vaporizer cylinder" portion is sawed in two with a metal cutting saw, the saw cut being transverse and perpendicular to the valve stem ("metering pin") bore and through the mid point of the tapered section of the "vaporization cylinder" which supports the "outer seal" of this valve. The severed portion of the "vaporization cylinder" which contains the vaporization chamber is discarded. Third, the not discarded portion of the "vaporization cylinder" is welded into an opening in a process pipe or vessel so that the cut surface of the "vaporization cylinder" is approximately flush with the inside surface of the pipe or vessel. Fourth, the remaining not discarded portion of the valve is reassembled to the welded portion of the "vaporization cylinder". Carrier gas is flowed through the valve via the "sample tube connectors". The distal end of the "outer seal" of the valve extends about 1/16 of an inch beyond the cut surface of the "vaporization cylinder" which is believed to be advantageous in obtaining a representative sample of the process liquid contained in the pipe or vessel.

What is claimed is:

1. A process analysis method which is a new use for a process gas chromatography liquid injection valve of the type having a distal heated vaporization chamber portion, a sample chamber portion, a valve stem bore intersecting both chambers, a grooved valve stem positioned within the valve stem bore and a means for moving the valve stem back and forth in the valve stem bore, the vaporization chamber portion of the valve being removed and discarded, the remainder of the valve containing the remaining chamber portion being mounted on a process conduit containing a process liquid or being mounted on a process vessel containing a process liquid, the method comprising the steps of:
   (a) flowing a stream of carrier gas through the remaining chamber of the valve to an analyzer;
   (b) extending the valve stem from the valve so that the groove is positioned outside the valve and into the process liquid so that the process liquid can fill the groove in the valve stem; and
   (c) retracting the valve stem into the valve so that the groove is positioned within the remaining chamber so that the liquid in the groove can evaporate into the carrier gas and be carried to the analyzer.

2. The method of claim 1, further including the step of heating the stream of carrier gas flowing through the remaining chamber of the valve so that the liquid in the groove can evaporate more rapidly in step (c).

3. The method of claim 1, further including the step of heating the remaining chamber portion of the valve so that the liquid in the groove can evaporate more rapidly in step (c).

* * * * *